United States Patent [19]

Bollinger

[11] Patent Number: 4,740,518

[45] Date of Patent: Apr. 26, 1988

[54] 4H-BENZO(4,5)CYCLOHEPTA(1,2-B)THIO-PHENE DERIVATIVES

[75] Inventor: Pietro Bollinger, Bottmingen, Switzerland

[73] Assignee: Sandoz Ltd., Basel, Switzerland

[21] Appl. No.: 72,807

[22] Filed: Jul. 14, 1987

Related U.S. Application Data

[63] Continuation of Ser. No. 931,378, Nov. 14, 1986, abandoned, which is a continuation of Ser. No. 659,250, Oct. 10, 1984, abandoned.

[30] Foreign Application Priority Data

Oct. 13, 1983 [GB]  United Kingdom ............ 8327403
Dec. 27, 1983 [GB]  United Kingdom ............ 8332660

[51] Int. Cl.⁴ ............... A61K 31/38; C07D 333/74
[52] U.S. Cl. ................................ 514/443; 549/44
[58] Field of Search ...................... 514/443; 549/44

[56] References Cited

U.S. PATENT DOCUMENTS 4,137,323  1/1979  Bastian ........................ 514/443

FOREIGN PATENT DOCUMENTS 0115690  8/1984  European Pat. Off. ........ 548/250

7206898  11/1972  Netherlands .................. 514/443

Primary Examiner—A. Siegel
Attorney, Agent, or Firm—Gerald D. Sharkin; Robert S. Honor; Thomas O. McGovern

[57] ABSTRACT

α-[5H-dibenzo[a,d]cyclohepten-5-ylidene]-carboxylic acids e.g. of formula I

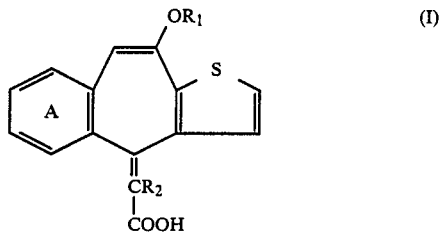

wherein $R_1$ is H, $C_{1-4}$alkyl or phenyl-($C_{1-4}$alkyl), $R_2$ is H or $C_{1-4}$alkyl and ring A is unsubstituted or halo- or hydroxy-substituted, as well as the physiologically-hydrolysable and -acceptable esters thereof have valuable pharmaceutical, in particular anti-inflammatory, antipyretic and analgesic properties.

16 Claims, No Drawings

4H-BENZO(4,5)CYCLOHEPTA(1,2-B)THIOPHENE DERIVATIVES

This is a continuation of application Ser. No. 931,378, filed Nov. 14, 1986, now abandoned, which in turn is a continuation of application Ser. No. 659,250, filed Oct. 10, 1984, now abandoned.

The present invention relates to novel 4H-benzo[4,5-]cyclohepta[1,2-b]thiophene derivatives having valuable pharmacological properties as well as to processes for their production, their use as pharmaceuticals and pharmaceutical compositions containing them.

European patent publications Nos. 0 035 903 and 0 115 690 and U.S. Pat. No. 4,376,124 relate to certain α-[5H-dibenzo[a,d]cyclohepten-5-ylidene]-carboxylic acids, disclosed as having anti-inflammatory as well as immunomodulatory activity. In Acta. Cryst. 37, 279–281 (1981) and Spanish Pat. No. 497 898 the compound [9,10-dihydro-4H-benzocyclohepta[1,2-b]thiophen-4-ylidene]-acetic acid is disclosed and described as an intermediate in the synthesis of tetracyclic compounds stated to possess CNS-activity.

The present invention relates to α-[10-oxy-4H-benzo[4,5]cyclohepta[1,2-b]thiophen-4-ylidene]-carboxylic acids, esters and salts. These compounds, which are novel and which are based on a cyclic system which is structurally remote from that of the product compounds of the references discussed above, have been found to possess particularly advantageous anti-inflammatory as well as anti-pyretic and analgesic activity as hereinafter described. Compounds of the invention have also been found to exhibit reduced occurrence of undesirable side effects, in particular ulcerogenicity, as compared with other, known anti-inflammatory agents.

In accordance with the foregoing the present invention provides: an α-[10-oxy-4H-benzo[4,5]cyclohepta[1,2-b]thiophen-4-ylidene]carboxylic acid or physiologically-hydrolysable and -acceptable ester or salt thereof.

It will be appreciated that the 4H-benzo[4,5]cyclohepta[1,2-b]thiophene nucleus in the compounds of the invention may bear substituents in addition to those specified at the 4- and 10-positions. In particular they may be further substituted in the benzene and/or in the thiophene ring. Thus apart from the substituents at the 4- and 10-positions, the 4H-benzo[4,5]cyclohepta[1,2-b]thiophene nucleus may for example be unsubstituted or substituted, e.g. mono-substituted, in the benzene ring by halogen, e.g. chlorine, or hydroxy.

In a specific embodiment the present invention provides a compound of formula I

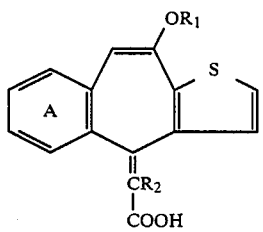

wherein
$R_1$ is hydrogen, $C_{1-4}$alkyl or phenyl-($C_{1-4}$alkyl),
$R_2$ is hydrogen or $C_{1-4}$alkyl, and
ring A is unsubstituted or halo- or hydroxy-substituted, or a physiologically-hydrolysable and -acceptable ester or a salt thereof.

Alkyl groups as $R_1$ and $R_2$ as well as alkyl moieties of phenyl($C_{1-4}$alkyl) groups as $R_1$ may be branched or straight-chain. When $R_1$ is $C_{1-4}$alkyl this is especially methyl. When $R_1$ is phenyl($C_{1-4}$alkyl) this is especially benzyl. Preferably $R_1$ is $C_{1-4}$alkyl. $R_2$ is preferably hydrogen. Ring A is preferably unsubstituted or mono-hydroxy or mono-halo (e.g. mono-chloro) substituted. Most preferably ring A is unsubstituted.

By the term "physiologically-hydrolysable and -acceptable ester" as applied to the compounds of the invention, e.g. the compounds of formula I, is meant esters in which the carboxylic group is esterified and which are hydrolysable under physiological conditions to yield an alcohol which is itself physiologically acceptable, e.g. non-toxic at desired dosage levels. Such esters include e.g. esters with aliphatic alcohols having 1 to 4 carbon atoms.

Salts of the compounds of the invention, e.g. of the compounds of formula I, include in particular their pharmaceutically acceptable salts. Such pharmaceutically acceptable salts include e.g. alkali metal salts such as the sodium and potassium salts, as well as alkaline earth metal salts such as the calcium salts.

It will be appreciated that compounds of the invention wherein the 10-oxy group is 10-hydroxy, e.g. compounds of formula I, wherein $R_1$ is hydrogen, exist in both keto as well as in enol form, e.g. in the case of compounds of formula I as tautomers of formula I′

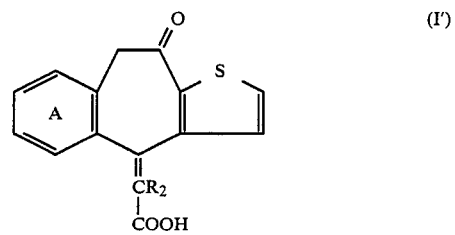

wherein $R_2$ and ring A are as defined above.

It is to be understood that where tautomeric forms occur, the present invention embraces both keto and enol forms, i.e. although compounds of the invention are defined for convenience by reference to the enol form only, the invention is not to be understood as being in any way limited by the particular nomenclature or graphic representation employed. Similar considerations apply in relation to starting materials exhibiting keto/enol-tautomerism as hereinafter described.

The compounds of the invention, e.g. compounds of the formula I, exist in both cis and trans isomeric forms, i.e. as Z and E isomers. The present invention is to be understood as embracing both the individual cis and trans isomers as well as mixtures thereof. In the present specification and claims cis (Z) and trans (E) isomers are designated in accordance with conventional CIP-nomenclature [Angew. Chem. 94, 614 (1982) and Loc. cit.]. Thus the cis isomer is the isomer of formula I″ and the trans isomer the isomer of formula I‴

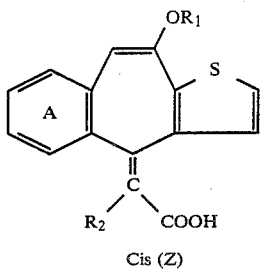

Cis (Z)

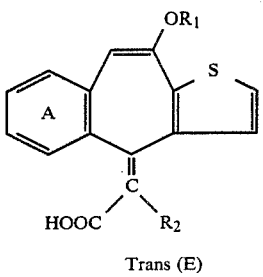

Trans (E)

In general, the cis (Z) isomers are preferred. Accordingly the compounds of the invention are preferably in predominantly cisform. Most preferably they are in pure or substantially pure cis form.

Individual cis and trans isomers of compounds of the invention may be obtained in accordance with techniques known in the art, e.g. by separation of cis/trans isomer mixtures, for example as hereinafter described in examples 4 and 5.

The present invention also provides a process for the production of compounds in accordance with the present invention, which process comprises:

(a) for the production of a physiologically-hydrolysable and -acceptable ester of an α-[10-oxy-4H-benzo[4,5-]cyclohepta[1,2-b]thiophene-4-ylidene]-carboxylic acid e.g. a compound of formula Ia

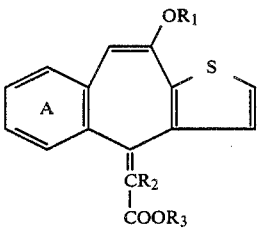

wherein $R_1$, $R_2$ and ring A are as defined above and $R_3$ is $C_{1-4}$alkyl, reacting a 10-oxy-4H-benzo-[4,5]cyclohepta[1,2-b]thiophen-4-one, for example a compound of formula II

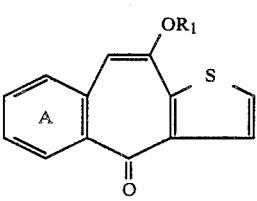

wherein $R_1$ and ring A are as defined above, under HORNER reaction conditions, with an appropriate oxycarbonylmethylen-phosphonate, for example a compound of formula III

wherein $R_2$ and $R_3$ are as defined above and $R_4$ is $C_{1-4}$alkyl or benzyl;

(b) for the production of an α-[10-oxy-4H-benzo[4,5-]cyclohepta[1,2-b]thiophen-4-ylidene]-carboxylic acid, for example a compound of formula I as defined above, hydrolysing an α-[10-oxy-4H-benzo[4,5]cyclohepta[1,2-b]thiophen-4-ylidene]-carboxylic acid ester (e.g. $C_{1-4}$alkyl ester), for example an ester of a compound of formula I as defined above (e.g. a compound of formula Ia as defined above);

(c) for the production of an α-[10-hydroxy-4H-benzo[4,5]cyclohepta[1,2-b]thiophen-4-ylidene]-carboxylic acid or $C_{1-4}$alkyl ester thereof, for example a compound of formula I or Ia as defined above wherein $R_1$ is hydrogen, subjecting an α-[10-($C_{1-4}$alkoxy)-4H-benzo[4,5]cyclohepta[1,2-b]thiophen-4-ylidene]-carboxylic acid or $C_{1-4}$alkyl ester thereof, for example a compound of formula I or Ia as defined above wherein $R_1$ is $C_{1-4}$alkyl, to ether cleavage;

(d) converting an α-[10-oxy-4H-benzo[4,5]cyclohepta[1,2-b]thiophen-4-ylidene]-carboxylic acid, for example a compound of formula I as defined above, into a physiologically-hydrolysable and -acceptable ester thereof, for example into a compound of formula Ia as defined above; and recovering an α-[10-oxy-4H-benzo[4,5]cyclohepta[1,2-b]thiophen-4-ylidene]-carboxylic acid, for example a compound of formula I as defined above, thus obtained in free form or in salt form.

Process step (a) above may be carried out in conventional manner, e.g. by reaction of (II) with (III) in the presence of a base such as dry NaH with concommitant formation of the III-ylid. The reaction is suitably conducted in an inert solvent or diluent such as dimethylsulfoxide at a temperature of from e.g. 50° to 120° C., under an inert atmosphere. As will be appreciated the oxycarbonyl moiety of the oxycarbonylmethylenphosphate starting material provides the ester moiety in the product compound. Appropriate oxycarbonylmethylenphosophonate starting materials are accordingly those wherein the said oxycarbonyl moiety represents a physiologically-hydrolysable and -acceptable ester residue in the product compound, and wherein the oxy moiety is other than hydroxy. The starting materials, e.g. of formula II for use in this process are known [see e.g. Helv. Chim. Acta 59, p 66–77 (1976) and DOS No. 26 25 642] or may be produced analogously to the known compounds. Conveniently the 10-oxy group in the starting material, e.g. in the case of compounds of formula II, the group $R_1O-$, will be other than hydroxy in order to avoid possible unwanted reaction at this position. Suitably the 10-oxy group, e.g. $R_1O-$ in formula II, is $C_{1-4}$alkoxy. Where such starting materials are employed and end-products are required having a 10-hydroxy group, these are suitably obtained e.g. by subsequent application of process step (c).

Process (b) may be carried out by any of the techniques known in the art for the hydrolysis of esters, for example by alkaline hydrolysis, e.g. in the presence of an alkali metal hydroxide at a temperature of from e.g.

20° C. to reflux in the presence of an inert solvent or diluent such as ethanol. $C_{1-4}$alkyl ester starting materials employed in process step (b) may be prepared in accordance with process step (a). Other esters suitable as starting materials may be prepared analogously.

Process step (c) may be carried out using any appropriate technique known in the art for the cleavage of enol-ether groups, for example by treatment with an appropriate organic or inorganic acid, e.g. a mineral acid such as $H_2SO_4$, HCl, HBr or phosphoric acid, or strong organic acids such as trifluoroacetic acid as well as aliphatic and aromatic sulfonic acids. The reaction is suitably carried out e.g. in an inert organic solvent such as tetrahydrofuran at a temperature of from e.g. 20° to 70°.

Conversion of initially obtained compounds, eg. of formula I, to physiologically-hydrolysable and -acceptable esters in accordance with process step (d) may be carried out by conventional techniques, for example as hereinafter described in example 3. When the 10-oxy group in the starting material is other than hydroxy, e.g. when compounds of formula I wherein $R_1$ is $C_{1-4}$alkyl are employed as starting materials, esterification may be accompanied by cleavage of this group, so that where end-products are required having the same 10-oxy group as the starting material yields may be reduced. Cleavage at the 10-position may however be reduced by selection of appropriate esterification techniques, e.g. proceeding via the corresponding acid chloride as intermediate.

The following examples are illustrative of the process of the present invention.

EXAMPLE 1

[10-Methoxy-4H-benzo[4,5]cyclohepta[1,2-b]thiophen-4-ylidene]-acetic acid ethyl ester (a) 21.6 g pre-dried NaH are suspended in 0.9 l dimethylsulfoxide and 200 g ethoxycarbonylmethylendiethylphosphonate [$(C_2H_5O)_2POCH_2COOC_2H_5$] are added drop-wise over ca. 1 hour, the temperature being maintained at ca. 25°–30° C. by light cooling. The obtained mixture is then stirred for 30 minutes at room temperature and 121 g 10-methoxy-4H-benzo[4,5]cyclohepta[1,2-b]thiophen-4-one dissolved with warming in 0.9 l dimethylformamide are then added in a single portion. The obtained reaction mixture is stirred for ca. 17 hours at ca. 95° C. under argon, and then stirred into a mixture of 7 l $H_2O$/3 kg ice and 50 ml conc. HCl covered with a layer of 2 l ethylacetate. The organic phase is separated off and the aqueous phase extracted 3× with 2 l and 3× with 1 l ethyl acetate. The combined organic phases are washed 3× with 2 l $H_2O$ and 3× with 2 l saline, dried with $MgSO_4$, filtered under suction and concentrated on a rotary evaporator to yield the title compound as a (Z,E)-isomer mixture: m.p.=91°–93° C.

The following compounds may be prepared as (Z,E)-isomer mixtures analogously:

(b) [7-Chloro-10-methoxy-4H-benzo[4,5]cyclohepta[1,2-b]thiophen-4-ylidene]-acetic acid ethyl ester (obtained as an oil).

(c) [6-Hydroxy-10-methoxy-4H-benzo[4,5]cyclohepta[1,2-b]thiophen-4-ylidene]-acetic acid ethyl ester.

EXAMPLE 2

[10-Methoxy-4H-benzo[4,5]cyclohepta[1,2-b]thiophen-4-ylidene]-acetic acid 200 g of the product of example 1a in 0.6 l ethanol are heated under reflux at 90° C. for 18 hours with 1.5 mol (60 g in 300 ml $H_2O$) NaOH. The obtained reaction mixture is concentrated to ⅓ volume in a rotary evaporator and the concentrate stirred with ca. 5 l $H_2O$/1 kg ice, and then extracted 2× each time using 2 l ethylether. The alkaline extract is re-extracted with 1 l 1N NaOH. The combined aqueous phases are taken up in 2 l ethylacetate and adjusted to ca. pH 1 by addition of dilute HCl with stirring. The organic phase is separated and extracted 4× each time using 1 l ethylacetate. The combined organic phases are washed 2× with saline, dried over $MgSO_4$ and evaporated to yield the title compound as a (Z,E) isomer mixture: m.p.=163°–167° C.

EXAMPLE 3

[10-Methoxy-4H-benzo[4,5]cyclohepta[1,2-b]thiophen-4-ylidene]-acetic acid methyl ester 2 g of the product of example 2 are suspended in 20 ml ethyl ether and a freshly prepared solution of diazomethane is added at 0° C. until $N_2$ evolution ceases. The solvent is evaporated off at 10° C. and the residue recrystallised from ethanol to yield the title compound as a (Z,E) isomer mixture: m.p.=124°–125° C.

EXAMPLE 4

[10-Methoxy-4H-benzo[4,5]cyclohepta[1,2-b]thiophen-4-ylidene]-acetic acid methyl ester (separation of isomers)

(a) The isomer mixture obtained in accordance with example 3 is separated chromatographically employing silica gel 60 H (Merk)—particle size=15 μm—and 98.5% toluene/1.5% dimethoxy ethane as eluant.

The (Z) isomer migrates in advance of the (E) isomer and is collected first.

M.P. for the (Z) isomer=124°–125° C.
M.P. for the (E) isomer=116°–117° C.
The following compounds may be prepared analogously starting from the products of examples 1b and 1c:

(b$^1$) (Z)-[7-Chloro-10-methoxy-4H-benzo[4,5]cyclohepta[1,2-b]thiophen-4-ylidene]-acetic acid ethyl ester: m.p.=118°–123° C.

(b$^2$) (E)-[7-Chloro-10-methoxy-4H-benzo[4,5]cyclohepta[1,2-b]thiophen-4-ylidene]-acetic acid ethyl ester: oil.

(c$^1$) (Z)-[6-Hydroxy-10-methoxy-4H-benzo[4,5]cyclohepta[1,2-b]thiophen-4-ylidene]-acetic acid ethyl ester.

(c$^2$) (E)-[6-Hydroxy-10-methoxy-4H-benzo[4,5]cyclohepta[1,2-b]thiophen-4-ylidene]-acetic acid ethyl ester.

EXAMPLE 5

[10-Methoxy-4H-benzo[4,5]cyclohepta[1,2-b]thiophen-4-ylidene]-acetic acid (individual cis- and trans-isomers)

(a$^1$) The individual (E) and (Z) isomer products obtained in accordance with example 4a are hydrolysed by dissolving in ethanol (1 l/Mol), addition of NaOH (1.5 Mol/Mol) and refluxing for 18 hours. The initially obtained reaction mixtures is evaporated to ⅓ volume under vacuum and poured into 1 kg ice/Mol. The aqueous phase is adjusted to pH 1 by the addition of HCl and the whole is extracted with 2 l/Mol ethyl acetate. The organic phase is washed with $H_2O$, dried over $MgSO_4$ and evaporated under reduced pressure to yield the individual (E) and (Z) isomer products.

M.P. for the (Z) isomer = 184°–187° C.
M.P. for the (E) isomer = 168°–171° C.

($a^2$) Alternatively the (Z) isomer may be obtained directly from the isomer mixture produced in example 2 in accordance with the following procedure.

The isomer mixture product of example 2 is dissolved in 1 l boiling 95% ethanol, seeded with crystals of the pure (Z) isomer obtained in accordance with example ($5a^1$) above and allowed to cool slowly with stirring. After standing for 20 hours the yellow crystal mass is filtered off and pressed. The pure (Z)-[10-methoxy-4H-benzo[4,5]cyclohepta[1,2-b]thiophen-4-ylidene]-acetic acid is obtained following re-crystallisation from ethanol: m.p. = 184°–187° C.

The following compounds may be prepared analogously to example $5a^1$ above.

($b^1$) (Z)-[7-Chloro-10-methoxy-4H-benzo[4,5]cyclohepta[1,2-b]thiophen-4-ylidene]-acetic acid: m.p. = 188°–191° C.

($b^2$) (E)-[7-Chloro-10-methoxy-4H-benzo[4,5]cyclohepta[1,2-b]thiophen-4-ylidene]-acetic acid: m.p. = 184°–187° C.

($c^1$) (Z)-[6-Hydroxy-10-methoxy-4H-benzo[4,5]cyclohepta[1,2-b]thiophen-4-ylidene]-acetic acid: Mass Spectrometry—Mol. Mass = 300.
NMR(360 MHz) in $CDCl_3$: H-$C_5$, bs, $\delta$ = 6.99; H-$C_9$, s, $\delta$ = 6.10; HO—CO—CH=, s, $\delta$ = 5.96.

($c^2$) (E)-[6-Hydroxy-10-methoxy-4H-benzo[4,5]cyclohepta[1,2-b]thiophen-4-ylidene]-acetic acid: Mass Spectrometry—Mol. Mass = 300.
NMR (360 MHz) in $CDCl_3$: H-$C_5$, bs, $\delta$ = 6.92; H-$C_9$, s, $\delta$ = 6.13; HO—CO—CH=, s, $\delta$ = 5.92; [$\delta$ in p.p.m.; s = singlet, bs = broadsinglet].

EXAMPLE 6

[10-Hydroxy-4H-benzo[4,5]cyclohepta[1,2-b]thiophen-4-ylidene]-acetic acid 1 g of the cis isomer product of example 5 is dissolved in tetrahydrofuran and 1N HCl is then added until the solution becomes turbid. The reaction mixture is refluxed for 2.5 hours and the organic solvent then evaporated off under reduced pressure. The remaining aqueous phase is extracted with ethyl acetate and the organic phase separated, washed with brine, dried over $MgSO_4$ and evaporated under reduced pressure. The residue is recrystallised from dichloromethane/hexane to yield the title compound in the form of the pure (Z) isomer: M.P. = 203°–208° C.

Compounds in accordance with the present invention and pharmaceutically acceptable salts thereof, e.g. compounds of formula I and their physiologically-hydrolysable and -acceptable esters and pharmaceutically acceptable salts, exhibit pharmacological activity and are therefore useful as pharmaceuticals.

In particular they exhibit anti-inflammatory activity, e.g. as indicated in (A) *THE ADJUVANT ARTHRITIS TEST IN THE RAT*. For this test adjuvant arthritis is induced according to the method of Pearson and Wood, "Arthr. Rheum."2, 440 (1959). Compounds of the invention, e.g. compounds of formula I, are active in this test against developing and established arthritis at dosages of from 5 to 30 mg/kg/day.

They also exhibit anti-pyretic activity, e.g. as indicated in (B) *THE YEAST-INDUCED FEVER TEST IN THE RAT*. For this test male rats (Sprague-Dawley) of 130-180 g are fasted overnight. Body temperature is measured the following morning using a thermistor rectal probe connected to a telethermometer. 1 ml/100 g body weight of a 15% suspension of dried baker's yeast in saline is then injected s.c.. Body temperature is measured 2 hours later and this value taken as the initial temperature. 6 hours after yeast injection the test animals receive an oral dosage of the test substance suspended in 0.5% tragacanth or tragacanth alone (control). Body temperature is again measured after a further 2 hours.

Increase in temperature for each rat is calculated and expressed as a % of average increase determined in the control group (ca. 2.3° C. above normal). The $ED_{50}$, estimated by regression analysis, is taken as the dosage at which increase in rectal temperature is 50% of that in the control group. Compounds of the invention, e.g. compounds of formula I, are active in this test at dosages of from 15 to 60 mg/kg.

They also exhibit analgesic activity, e.g. as indicated in (C) *THE ARTHRITIS PAIN TEST IN THE RAT*. For this test male rats (OFA) of 110-120 g are treated with 0.1 ml of a Mycobacterium butyricum suspension in paraffin oil (0.6 mg Mycobact./0.1 ml oil) injected i.c. into the tail root. Marked arthritis in the hind-paws develops ca. 12 days after treatment. 30 mins. before administration of test-substance, control measurement is performed by flexing the foot joint of the right or left hind-paw using a Statham transducer until vocalisation occurs. Rats which do not vocalise are discarded. Test substance is administered orally and the flexion procedure repeated 1,3 and 5 hours subsequently. The pressure at which vocalisation occurs is noted, the value recorded for each rat at each interval being the average value of three successive measurements. Animals in which the vocalisation threshold is doubled with respect to the control measurement are considered to be protected. The $ED_{50}$ estimated for each post-treatment time according to the Probit method is taken as the dosage at which 50% of animals are protected. Compounds of the invention, e.g. compounds of formula I, are active in this test at dosages of from 3.2 to 100 mg/kg.

In view of their anti-inflammatory activity, the said compounds [i.e. compounds of the invention and pharmaceutically acceptable salts thereof, e.g. compounds of formula I and their physiologically-hydrolysable and -acceptable esters and pharmaceutically acceptable salts] are useful for the treatment of inflammation, e.g. for the treatment of arthritis and rheumatic diseases such as polyarthritis chronica progediens, as well as other chronic inflammatory conditions where anti-arthritic treatment is indicated.

In view of their anti-pyretic activity, the said compounds are also useful as fever-controlling or reducing agents, e.g. for use in reduction of fever associated with infectious disease or in other conditions where supportive, anti-pyretic therapy is indicated.

In view of their analgesic activity, the said compounds are further useful as analgesic agents, in particular in the treatment of pain associated with inflammatory conditions.

The said compounds may be administered by any conventional route, in particular enterally, especially orally in the form of e.g. tablets or capsules. They may also be administered parenterally e.g. in the form of injectible solutions or suspensions.

For the above usages the required dosage will of course vary depending on the mode of administration, the particular condition to be treated and the therapy desired. In general however satisfactory results are obtained on administration of compounds of the invention at a daily dosage of from about 5 to about 30 mg/kg animal body weight, p.o. for anti-inflammatory and analgesic effect and from about 15 to about 60 mg/kg animal body weight, p.o. for anti-pyretic effect.

For larger mammals an indicated total daily dosage is in the range of from about 350 mg to about 2.0 g, for anti-inflammatory and analgesic effect and from about 1.0 to about 4.0 g, for anti-pyretic effect, conveniently administered once or in divided doses 2 to 4 times a day, or in retard form. Dosage forms suitable for oral administration accordingly comprise from about 80 mg to about 1.0 g, (anti-inflammatory/analgesic) or from about 250 mg to about 2.0 g (anti-pyretic) active ingredient admixed with a solid or liquid pharmaceutical diluent or carrier therefor.

In connection with the above described uses it is to be particularly noted that compounds of the invention, e.g. compounds of formula I, have surprisingly been found to exhibit substantially reduced side effects, in particular ulcerogenicity, as compared with other known non-steroidal anti-inflammatory agents.

As noted above, a suitable daily dosage for any specific compound in accordance with the invention will depend on its relative potency. For the preferred compound in accordance with the invention, [10-methoxy-4H-benzo[4,5]cyclohepta[1,2-b]thiophen-4-ylidene]-acetic acid (compound A in the table below), results obtained in test A, B and C compared with acetylsalicyclic acid (Aspirin) (compound B in the table below), are as follows:

for use as an anti-inflammatory, anti-pyretic or analgesic agent;

(ii) A method of treating inflammation, or of controlling or reducing fever, or of alleviating pain in a subject in need of such treatment, which method comprises administering to said subject an anti-inflammatorily, anti-pyretically or analgesically effective amount of an α-[10-oxy-4H-benzo[4,5]cyclohepta[1,2-b]thiophen-4-ylidene]-carboxylic acid (e.g. of a compound of formula I as hereinbefore defined), or physiologically-hydrolysable and -acceptable ester or pharmaceutically acceptable salt thereof; as well as (iii) A pharmaceutical composition comprising an α-[10-oxy-4H-benzo[4,5]cyclohepta[1,2-b]thiophen-4-ylidene]-carboxylic acid (e.g. a compound of formula I as hereinbefore defined), or physiologically-hydrolysable and -acceptable ester or pharmaceutically acceptable salt thereof, together with a pharmaceutically acceptable diluent or carrier therefor.

I claim:

1. A compound of formula I

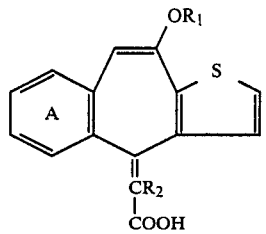

wherein
$R_1$ is hydrogen, $C_{1-4}$alkyl or phenyl-($C_{1-4}$alkyl),
$R_2$ is hydrogen or $C_{1-4}$alkyl, and
ring A is unsubstituted or halo- or hydroxy-substituted,
or a physiologically-hydrolysable and -acceptable ester or a pharmaceutically acceptable salt thereof.

2. A compound according to claim 1 which is [10-

|  | TEST A | | TEST B | TEST C |
|---|---|---|---|---|
|  | DEVELOPING ARTHRITIS | ESTABLISHED ARTHRITIS | YEAST FEVER | ARTHRITIS PAIN |
| COMPOUND | ED₅₀ (mg/kg/day) | | ED₅₀ (mg/kg) | ED₅₀ (mg/kg) |
| A | 15[1]/8[2] | 15[1]/16[2] | 22[2] | 7[2] |
| B | 140 | 240 | 161 | 90 |

[1]result obtained using cis/trans (Z,E) isomer mixture.
[2]result obtained using cis (Z) isomer.

Indicated daily dosages for compound A in accordance with the invention in relation to anti-inflammatory therapy will accordingly be of the order of 1/10 to 1/15 in the case of the isomer mixture, or 1/15 in the case of the pure cis-isomer, of those commonly employed using acetylsalicyclic acid as medication.

In relation to anti-pyretic and analgesic therapy, daily dosages for compound A in the form of the cis-isomer will be of the order of 1/7 and 1/12 respectively of those commonly employed using acetylsalicyclic and as medication.

In accordance with the foregoing of the present invention further provides:

(i) An α-[10-oxy-4H-benzo[4,5]cyclohepta[1,2-b]thiophen-4-ylidene]-carboxylic acid, (e.g. a compound of formula I as hereinbefore defined), or physiologically-hydrolysable and -acceptable ester or pharmaceutically acceptable salt thereof, for use as a pharmaceutical, e.g.

hydroxy-4H-benzo[4,5]cyclohepta[1,2-b]thiopen-4-ylidene]-acetic acid, or a physiologically-hydrolysable and -acceptable ester or a pharmaceutically acceptable salt thereof.

3. A compound of formula I

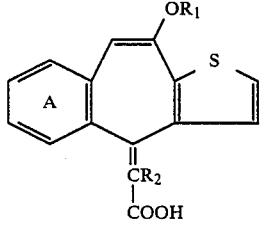

wherein
$R_1$ is $C_{1-4}$alkyl $R_2$ is hydrogen, and ring A is unsubstituted or halo- or hydroxy-substituted, or a physiologically-hydrolysable and -acceptable ester or a pharmaceutically acceptable salt thereof.

4. A compound according to claim 3 which is [10-methoxy-4H-benzo[4,5]cyclohepta[1,2-b]thiophen-4-ylidene]-acetic acid, or a physiologically-hydrolysable and -acceptable ester or a pharmaceutically acceptable salt thereof.

5. A compound according to claim 3 which is a compound selected from the group consisting of:
   (a) [10-Methoxy-4H-benzo[4,5]cyclohepta[1,2-b]thiophen-4-ylidene]-acetic acid;
   (b) [7-Chloro-10-methoxy-4H-benzo[4,5]cyclohepta[1,2-b]thiophen-4-ylidene]-acetic acid;
   (c) [6-Hydroxy-10-methoxy-4-benzo[4,5]cyclohepta[1,2-b]thiophen-4-ylidene]-acetic acid;
   (d) The physiologically-hydrolysable and -acceptable esters and pharmaceutically acceptable salts of acids as defined under (a) to (c) above.

6. A compound according to claim 3 in predominantly cis form.

7. A compound according to claim 6 in pure or substantially pure cis form.

8. A compound according to claim 4 which is (Z)-[10-methoxy-4H-benzo[4,5]cyclohepta[1,2-b]thiophen-4-ylidene]-acetic acid, or a pharmaceutically acceptable salt thereof.

9. A pharmaceutical composition comprising an α-[10-oxy-4H-benzo[4,5]cyclohepta[1,2-b]thiophen-4-ylidene]-carboxylic acid as claimed in claim 3 or a physiologically-hydrolysable and -acceptable ester or a pharmaceutically acceptable salt thereof, together with a pharmaceutically acceptable diluent or carrier therefore.

10. A method of treating inflammation in a subject in need of such treatment, which method comprises administering to said subject an anti-inflammatorily effective amount of an α-[10-oxy-4H-benzo[4,5]cyclohepta[1,2-b]thiophen-4-ylidene]-carboxylic and as defined in claim 3 or of a physiologically-hydrolysable and -acceptable ester or pharmaceutically acceptable salt thereof.

11. A method of treating, controlling or reducing fever in a subject in need of such treatment, which method comprises administering to said subject an antipyretically effect amount of an α-[10-oxy-4H-benzo[4,5-]cyclohepta[1,2-b]thiophen-4-ylidene]-carboxylic acid as defined in claim 3 or of a physiologically-hydrolysable and -acceptable ester or pharmaceutically acceptable salt thereof.

12. A method of alleviating pain in a subject in need of such treatment, which method comprises administering to said subject an analgesically effective amount of an α-[10-oxy-4H-benzo[4,5]cyclohepta[1,2-b]thiophen-4-ylidene]-carboxylic acid as defined in claim 3 or of a physiologically-hydrolysable and -acceptable ester or pharmaceutically acceptable salt thereof.

13. A compound according to claim 4 in predominantly cis form.

14. A compound according to claim 4 in pure or substantially pure cis form.

15. A compound according to claim 5 in predominantly cis form.

16. A compound according to claim 5 in pure or substantially pure cis form.

* * * * *